United States Patent
Suwito et al.

(10) Patent No.: US 11,730,886 B2
(45) Date of Patent: Aug. 22, 2023

(54) SHAPED MEMORY POLYMER JUNCTIONS

(71) Applicant: CareFusion 303, Inc., San Diego, CA (US)

(72) Inventors: Wantjinarjo Suwito, West Linn, OR (US); Zehra Sevinc, Long Grove, IL (US)

(73) Assignee: CAREFUSION 303, INC., San Diego, CA (US)

( * ) Notice: Subject to any disclaimer, the term of this patent is extended or adjusted under 35 U.S.C. 154(b) by 476 days.

(21) Appl. No.: 15/930,209

(22) Filed: May 12, 2020

(65) Prior Publication Data

US 2021/0353855 A1    Nov. 18, 2021

(51) Int. Cl.
*A61M 5/168* (2006.01)
*A61M 5/34* (2006.01)
*A61M 39/10* (2006.01)

(52) U.S. Cl.
CPC ............ *A61M 5/168* (2013.01); *A61M 5/346* (2013.01); *A61M 5/349* (2013.01); *A61M 39/10* (2013.01); *A61M 2205/0266* (2013.01)

(58) Field of Classification Search
CPC ...... A61M 5/168; A61M 5/346; A61M 5/349; A61M 39/10; A61M 2205/0266
USPC ........................................................ 604/530
See application file for complete search history.

(56) References Cited

U.S. PATENT DOCUMENTS

| | | | |
|---|---|---|---|
| 5,772,261 A * | 6/1998 | Magram | A61M 27/002 604/8 |
| 6,152,914 A | 11/2000 | Van De Kerkhof et al. | |
| 2005/0137614 A1 | 6/2005 | Porter et al. | |
| 2006/0020242 A1 | 1/2006 | Yamazaki et al. | |
| 2008/0060175 A1 * | 3/2008 | Barvosa-Carter | B29C 65/66 24/442 |
| 2008/0114308 A1 | 5/2008 | di Palma et al. | |
| 2015/0362109 A1 * | 12/2015 | Buchanan | A61M 39/12 285/399 |

FOREIGN PATENT DOCUMENTS

| | | |
|---|---|---|
| EP | 3221628 A1 | 9/2017 |
| KR | 20190105231 A | 9/2019 |

(Continued)

OTHER PUBLICATIONS

International Search Report and Written Opinion for Application No. PCT/US2021/031844, dated Aug. 27, 2021, 16 pages.

(Continued)

*Primary Examiner* — Phillip A Gray (74) *Attorney, Agent, or Firm* — Morgan, Lewis & Bockius LLP (57) ABSTRACT

Junction assemblies for joining intravenous (IV) devices to tubing are provided. A junction assembly includes a component connector and a shaped memory polymer (SMP) member formed of a shape changing material. The junction assembly allows movement of the tube along the component connector when the SMP member is in an expanded state and the junction assembly retains the tube securely against the component connector when the SMP member is in a contracted state. The shape changing material changes to one of the expanded state and the contracted state upon being subjected to an external stimuli. Methods of assembling junction assemblies are also provided.

19 Claims, 3 Drawing Sheets

(56) References Cited

FOREIGN PATENT DOCUMENTS

| WO | WO-9637254 A2 * | 11/1996 | ............ A61M 39/12 |
| WO | WO-9822175 A1 | 5/1998 | |

OTHER PUBLICATIONS

Frankland, Jim, "EXTRUSION: Orientation: The Good and the Bad", Extrusion Know How, Published Jul. 29, 2016, https://www.ptonline.com/articles/extrusion-orientation-the-good-and-the-bad.

Garcia Rosales, et al., "Characterization of shape memory polymer parts fabricated using material extrusion 3D printing technique", Rapid Prototyping Journal, Emerald Publishing Limited, vol. 25 No. 2, Mar. 4, 2019, ISSN: 1255-2546, https://doi.org/10.1108/RPJ-08-2017-0157.

Hearon et al., "A Processable Shape Memory Polymer System for Biomedical Applications", Advanced Healthcare Materials, Apr. 30, 2015, vol. 4, Issue 9, https://doi.org/10.1002/adhm.201500156.

Lanzalaco et al., "Poly(N-isopropylacrylamide) and Copolymers" A Review on Recent Progresses in Biomedical Applications, Oct. 4, 2017, MDPI, Gels 2017, 3, 36; doi:10.3390/gels3040036, www.mdpi.com/journal/gels, 32 pages.

M. E. S. R. Silva, et al., "Miscibility Behavior of Polyacrylamides Poly(Ethylene Glycol) Blends: Flory Huggins Interaction Parameter Determined by Thermal Analysis", Scientific Research, Journal of Modern Physics, 2013, 4, 45-51, http://dx.doi.org/10.4236/jmp.2013.47A2007 Published Online Jul. 2013 (http://www.scirp.org/journal/jmp).

Polymer Properties Database, "Polynorbornenes (PNR)", CROW Polymer Properties Database, 2015, http://polymerdatabase.com/Elastomers/PNR.html.

SMP Technologies Inc., "Intelligent Material Able to Adjust Itself Accordingly to Ensure the Highest Level of Comfort & Affinity with Human Body", SMP Technologies Inc., 2018, 34 pages.

Wikipedia, "Poly(N-isopropylacrylamide)", Wikimedia Foundation, Inc., 2019, https://en.wikipedia.org/w/index.php?title=Poly(N-isopropylacrylamide)&oldid=906940791.

Zhao, et al., "4D printing of shape memory polyurethane via stereolithography", European Polymer Journal 101 (2018) 120-126, https://doi.org/10.1016/j.eurpolymj.2018.02.021.

\* cited by examiner

SHAPED MEMORY POLYMER JUNCTIONS

CROSS-REFERENCES TO RELATED APPLICATIONS

N/A

BACKGROUND

Infusion or intravenous (IV) sets are constructed by joining multiple translucent polymeric tubing segments to multiple polymeric components. The junctions are typically formed by applying a thin layer of solvent or adhesive on one or both of the contacting surfaces and then the two surfaces are brought together. The contacting surface of the tubing can either be at the inner diameter, the outer diameter, or both diameters up to a certain length from one end. The solvent/adhesive is applied either internally, externally, or both. The bonded area is a critical parameter that if not controlled can cause the tubing/component junction to leak or separate easily. The junctions are also sometimes formed by tightening a retaining ring to squeeze the tubing segment onto a component connector. The retaining ring is typically crimped or crushed after placement over the tubing/connector junction. The degree of the retaining force is also a critical parameter that can cause the tubing/component junction to leak or separate easily. The bond parameter and the retaining force can each vary significantly due to design shortfalls, assembly process shortfalls and process drifts.

The typical bonded/retained junction has several weaknesses, such as a low pull out force that causes the bonded/retained junction to separate and a low burst pressure that causes the bonded/retained junction to leak or rupture. It is desirable to provide for stronger junctions between IV tubing and IV components to increase the pull out force and burst pressure parameters, thereby minimizing leaks and separations.

SUMMARY

The present disclosure provides shape memory (SMP) polymer connectors for IV components used to provide a strong and consistent connection between an IV tube and an IV component when subjected to a particular external stimuli, such as temperature, thermal gradient and moisture.

In one or more embodiments, a junction assembly for an IV component is provided. The junction assembly includes a component connector having a spigot configured to slideably receive an inner surface of an IV tube to form a connector/tube junction and an SMP ring formed of a shape changing material. The SMP ring has an expanded state in which the SMP ring is slideably disposed encircling the connector/tube junction and a contracted state in which the SMP ring is retained in a retaining position squeezing the connector/tube junction. The shape changing material is configured to change to one of the expanded state and the contracted state upon being subjected to an external stimuli.

In one or more aspects, the spigot is sized and shaped to provide a friction fit with the inner surface of the IV tube. In one or more aspects, the spigot includes a barb, the barb sized and shaped to provide a friction fit with the inner surface of the IV tube. In one or more aspects, the barb has an outer circumference and the SMP ring has an inner diameter that is narrower than the outer circumference of the barb when the SMP ring is in the contracted state. In one or more aspects, one of a solvent bond and an adhesive bond is disposed between the spigot and the inner surface of the IV tube. In one or more aspects, the external stimuli is a change in temperature. In one or more aspects, the external stimuli is a change in moisture content.

In one or more aspects, the shape changing material is configured to be in the expanded state upon application of a lubricating assembly solvent and to be in the contracted state upon application of a temperature change. In one or more aspects, the shape changing material is an extruded thermo-responsive material that maintains the expanded state outside of an extrusion water bath, and wherein a cloud point of the thermo-responsive material is configured to shrink the thermo-responsive material to the contracted state upon losing moisture content when an increased temperature is applied. In one or more aspects, the shape changing material comprises Poly (N-isopropylacrylamide) (PNIPAAm) blended with one of EVA, Poly (ethylene glycol), TPU, TPE or melt processable polybutadiene. In one or more aspects, the shape changing material comprises a flexible PVC blend containing one of PP, EVA and LDPE. In one or more aspects, the shape changing material comprises a flexible TPE blend containing one of PP, EVA and LDPE.

In one or more embodiments, a junction assembly for an IV component is provided. The junction assembly includes an SMP connector formed of a shape changing material. The SMP connector includes a shaft configured to slideably receive an inner surface of an IV tube, a compression flange configured to slideably receive an outer surface of the IV tube, the shaft, the compression flange and the IV tube forming a connector/tube junction, and a gap disposed between the shaft and the compression flange. In an expanded state the compression flange is expanded and the gap at a tube insertion end of the SMP connector is a first width. In a contracted state the compression flange is narrowed and the gap at the tube insertion end of the SMP connector is a second width that is less than the first width. The shape changing material is configured to change to one of the expanded state and the contracted state upon being subjected to an external stimuli.

In one or more aspects, the compression flange is expanded into the expanded state by a force applied by an expansion tool, and wherein the compression flange is contracted into the contracted state by application of a change in temperature to the compression flange. In one or more aspects, the expanded state of the compression flange is a funnel shape and the contracted state of the compression flange is a cylindrical shape. In one or more aspects, a solvent bond and an adhesive bond is disposed between one of the shaft and the compression flange and the inner surface of the IV tube. In one or more aspects, the shape changing material comprises PNIPAAm blended with one of EVA, Poly (ethylene glycol), TPU or melt processable polybutadiene, and wherein a cloud point of the shape changing material is configured to shrink the shape changing material to the contracted state upon losing moisture content when an increased temperature is applied.

In one or more embodiments, an infusion set assembly is provided. The infusion set includes an IV set component, an IV tube and a junction assembly coupling the IV tube to the IV set component. The junction assembly includes a component connector configured to slideably receive an inner surface of the IV tube and an SMP member formed of a shape changing material. The junction assembly is configured to allow slideable movement of the IV tube with respect to the component connector when the SMP member is in an expanded state. The junction assembly is configured to retain the IV tube securely to the component connector when the SMP member is in a contracted state. The shape changing material is configured to change to one of the expanded state and the contracted state upon being subjected to an external stimuli.

In one or more aspects, the component connector includes a spigot with a barb and the SMP member is a ring, the ring having a first diameter in the expanded state, the first diameter being greater than a diameter of the IV tube encircling the widest portion of the barb and a second diameter in the contracted state, the second diameter being smaller than a diameter of the IV tube encircling the widest portion of the barb. In one or more aspects, the component connector is a shaft that engages an inner surface of the IV tube and the SMP member is a compression flange that engages an outer surface of the IV tube, the SMP member having a flared shape in the expanded state, wherein a gap between the shaft and the compression flange has a first width at a tube insertion end of the gap and a second width at a base of the gap, the first width being greater than the second width and a cylindrical shape in the contracted state, wherein the first width of the gap is the same as the second width of the gap.

Additional features and advantages of the disclosure will be set forth in the description below and, in part, will be apparent from the description or may be learned by practice of the disclosure. The objectives and other advantages of the disclosure will be realized and attained by the structure particularly pointed out in the written description and claims hereof as well as the appended drawings.

It is to be understood that both the foregoing general description and the following detailed description are exemplary and explanatory and are intended to provide further explanation of the disclosure as claimed.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Infusion sets may be formed from any combination of infusion components and tubing. Typically, the infusion components and tubing are disposable products that are used once and then discarded. The infusion components and tubing may be formed from any suitable material (e.g., thermoplastics, thermoplastic elastomers, silicone, and rubber). An issue in manufacturing infusion sets is consistently joining the tubing and the infusion components to obtain a secure and/or leak free joint with desired fluid flow. The joint may be formed at either the inner or outer diameter of the tubing.

A typical connection between IV components and IV tubing includes a standard IV tube connected to a hard (e.g., plastic, metal) IV component connector via an adhesive/solvent bond or a crimped retainer ring. In the case of an adhesive bond, an incomplete joining of the IV component connector and the IV tubing leaves a gap. In the case of the retainer ring, a great force is required to crimp the retainer ring over the IV tube onto the IV component connector. However, the pull out force of the crimped junction is relatively low (e.g., ~3.7 lbf) and the burst pressure of the crimped junction is also low (e.g., ~30 psi). Thus, both the typical adhesive bond junction and the typical crimped retainer ring junction are susceptible to leaks and separation.

Figure 1:
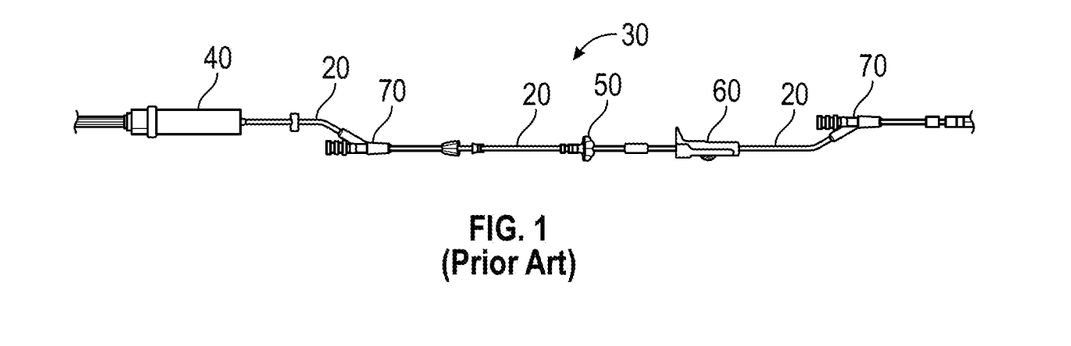
FIG. 1 is a schematic view of a typical assembled infusion set.

As shown in FIG. 1, a typical infusion set 30 may include a drip chamber 40, a check valve 50, a roller clamp 60 and Y-junctions 70, all connected together by tubing 20. A typical infusion set 30 can include additional infusion components and can be formed of any combination of components and the tubing 20.

Figure 2:
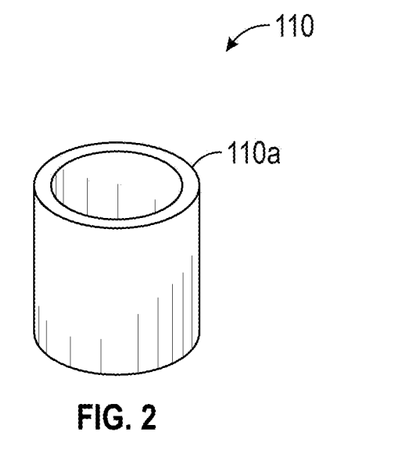
FIG. 2 is a perspective view of an SMP connector component in a constricted state, according to aspects of the disclosure.
Figure 3:
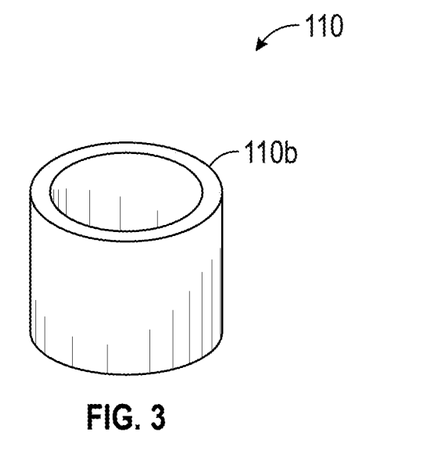
FIG. 3 is a perspective view of the SMP connector component of FIG. 2 in an expanded state, according to aspects of the disclosure.
Figure 4:
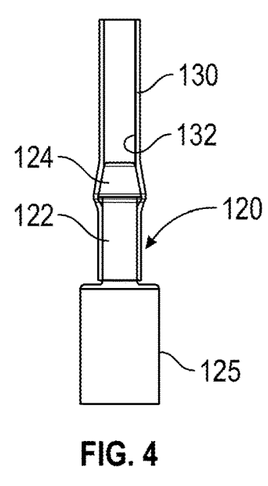
FIG. 4 is a front view of an IV component/tube junction, according to aspects of the disclosure.

As shown in FIGS. 2-6, an IV component/tube junction is shown as junction assembly 100. Junction assembly 100 includes an SMP ring 110 formed of an SMP material that expands or contracts based on an external stimuli (e.g., temperature, thermal, moisture). As shown in FIG. 1 the SMP ring 110 is in a contracted state 110a and as shown in FIG. 2 the SMP ring 110 is in an expanded state 100b. An IV component 125 (e.g., drip chamber, check valve) has a component connector 120 (e.g., drip chamber connector, check valve connector) that includes a spigot 122 sized and shaped to receive a tube 130 (e.g., IV tubing), where the spigot 122 slideably engages with an inner surface 132 of the tube 130. The tube 130 may require some level of force to slide onto the spigot 122 (e.g., friction fit). The component connector 120 may also include a barb 124 as shown in FIG. 4, though a barbless spigot is also contemplated in some aspects of the disclosure. The barb 124 may increase the friction fit of the tube 130 with the component connector 120.

Figure 5:
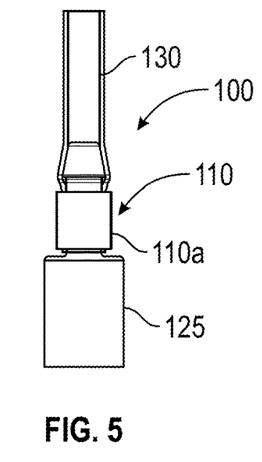
FIG. 5 is a front view of an IV component/tube junction assembly, according to aspects of the disclosure.
Figure 6:
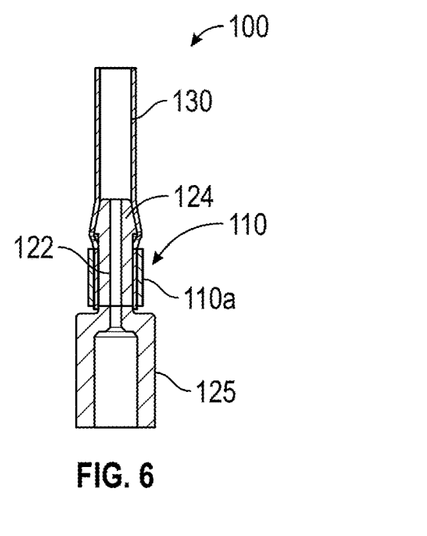
FIG. 6 is a cross-sectional front view of the IV component/tube junction assembly of FIG. 5, according to aspects of the disclosure.

In use, the SMP ring 110 in the expanded state is slideably moved along the tube 130 until the SMP ring 110 is disposed over the spigot 122. The SMP ring 110 must be expanded enough to fit over the tube 130 and the barb 124 of the spigot 122. As shown in FIG. 5, The SMP ring 110 is then subjected to the appropriate external stimuli to cause the SMP ring 110 to shrink to the contracted state, thus forcing (e.g., crushing, crimping, squeezing) the tube 130 against the spigot 122 to provide a bonded junction. The tube 130 is strongly retained by the junction assembly 100, thus requiring a higher pull out force and a higher burst pressure for failure than typical IV junctions due to a higher friction fit and a strong SMP ring 110, respectively.

Figure 7A:
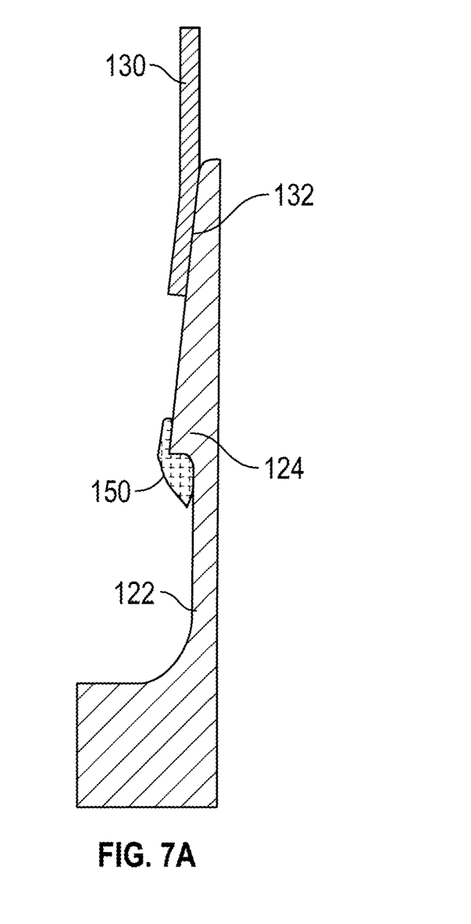
FIGS. 7A and 7B are cross-sectional partial front views of a component/tube junction with an adhesive bond, according to aspects of the disclosure.
Figure 7B:
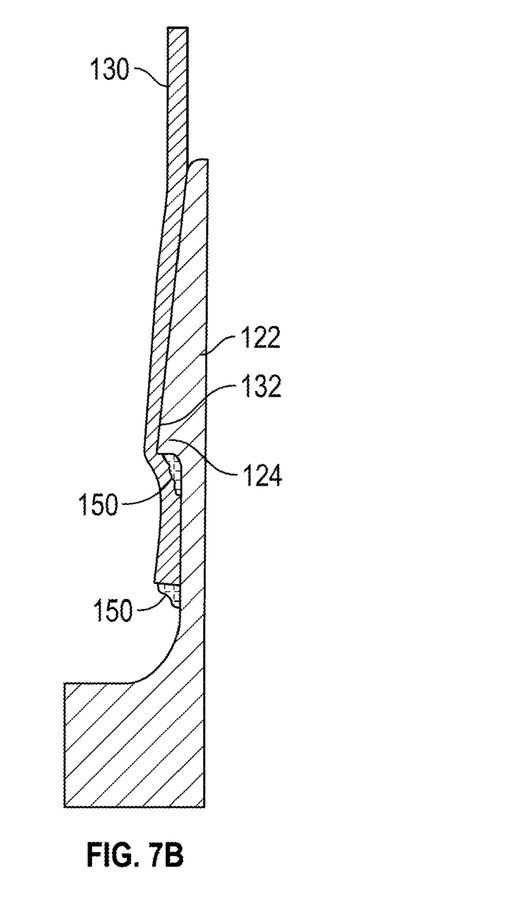

In some aspects of the disclosure, an even stronger bond between the tube 130 and the spigot 122 may be provided by adding a solvent/adhesive to the junction assembly 100. As shown in FIG. 7A, an axis symmetric cross section of a full 360 degree bond joint, an amount of a solvent/adhesive 150 may be applied to the barb 124 of the spigot 122 and the tube 130 may be engaged with the spigot 122. The solvent/adhesive acts as lubricant to reduce the peak insertion force of the tube. As shown in FIG. 7B, the tube 130 is slideably moved on the spigot 122 past the barb 124 so that the inner surface 132 of the tube 130 is engaged with the barb 124 and with portions of the spigot 122 before and after the barb 124. Here, a portion of the solvent/adhesive 150 is disposed between the inner surface 132 and a portion of the spigot 122 just past the barb 124, forming a mechanical hedge after cured and further preventing a tube pull out, and another portion of the solvent/adhesive 150 is disposed at the end of the tube 130 alongside a portion of the spigot 122, forming a complete seal if the tube end remains flared open.

In some aspects of the disclosure, the SMP ring 110 may be in the contracted state 110a prior to assembly, then subjected to an external stimuli to change to the expanded state 110b for assembly onto the tube 130 and the spigot 122, and then subjected to another external stimuli to change back to the contracted state 110a. For example, the SMP ring 110 may be in the contracted state 110a at room temperature, may change to the expanded state 110b when subjected to a particular temperature greater than room temperature and may change back to the contracted state 110a when the temperature cools back down to or below room temperature. In some aspects of the disclosure, the SMP ring 110 may be in the expanded state 110b prior to assembly (e.g., at room temperature) then subjected to an external stimuli (e.g., activation temperature) to change to the contracted state 110a.

As shown in FIGS. 8-12, an IV component/tube junction is shown as junction assembly 200. Junction assembly 200 includes an SMP connector 210 (e.g., IV component connector) formed of an SMP material that expands or contracts based on an external stimuli (e.g., temperature, thermal, moisture). The SMP connector 210 includes a shaft 212 (e.g., inner portion) sized and shaped to slideably engage with the inner surface 132 of the tube 130. The SMP connector 210 also includes a compression flange 214 (e.g., outer portion) sized and shaped to slideably engage with an outer surface 134 of the tube 130. Here, when the tube 130 is connected to or mated with the SMP connector 210, the tube 130 is sandwiched in a gap 216 between the shaft 212 and the compression flange 214.

Figure 8:
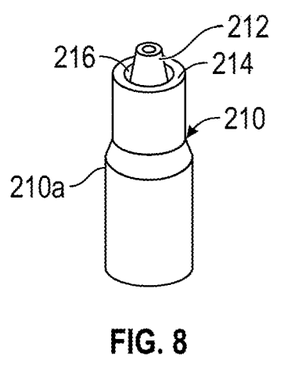
FIG. 8 is a perspective view of an SMP connector component in a constricted state, according to aspects of the disclosure.
Figure 9:
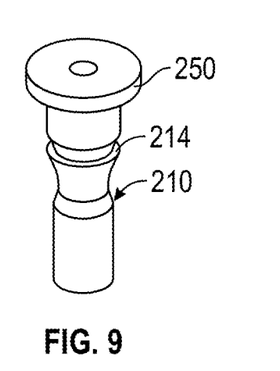
FIG. 9 is a perspective view of the SMP connector component of FIG. 8 engaged by a shaping tool, according to aspects of the disclosure.
Figure 10:
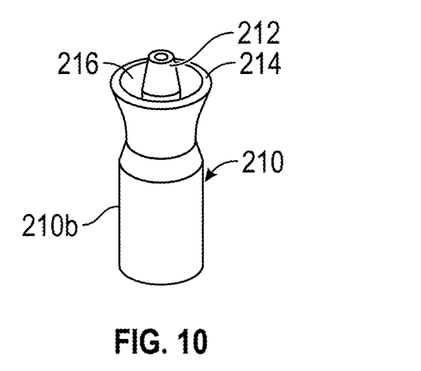
FIG. 10 is a perspective view of the SMP connector component of FIG. 8 in an expanded state, according to aspects of the disclosure.

As shown in FIG. 8 the SMP connector 210 is in a contracted state 210a. In the contracted state 210a, the compression flange 214 may be parallel with the shaft 212 such that the gap 216 is essentially uniform or consistent in thickness. As shown in FIG. 9, an expansion tool 250 (e.g., flaring tool) may be inserted into the SMP connector 210 and/or the SMP connector 210 may be forced onto the expansion tool 250, causing portions of the compression flange 214 to expand (e.g., flare out) away from the shaft 212. For example, the compression flange 214 may flare out in a funnel shape. The resulting shape causes the SMP connector 210 to be in an expanded state 210b, as shown in FIG. 10. Here, the gap 216 is wider at a tube insertion end 218 of the SMP connector 210 and the gap 216 narrows going away from the tube insertion end 218, where the deepest portion of the gap 216 may maintain the same width as in the contracted state 210a.

Figure 11:
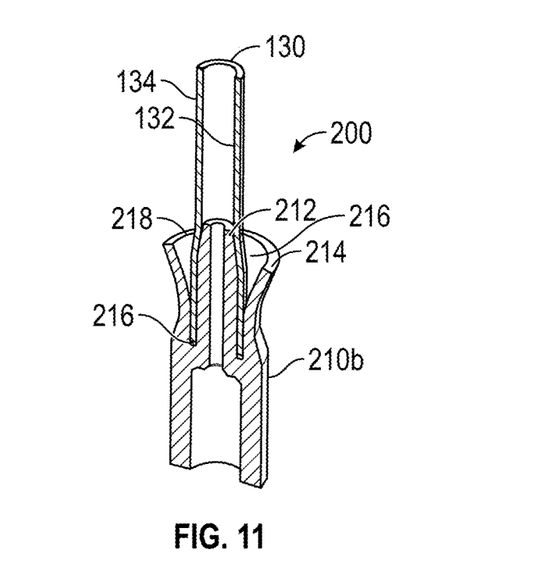
FIG. 11 is a cross-sectional perspective view of an IV component/tube junction in an expanded state, according to aspects of the disclosure.
Figure 12:
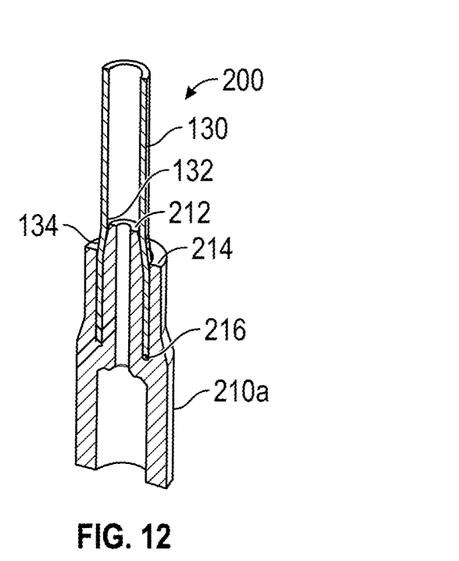
FIG. 12 is a cross-sectional perspective view of the IV component/tube junction of FIG. 11 in a contracted state, according to aspects of the disclosure.

In use, the tube 130 is slideably moved onto the SMP connector 210 in the expanded state 210b so that the tube 130 is disposed in the gap 216 between the shaft 212 and the compression flange 214, as shown in FIG. 11. An external stimuli (e.g., activation temperature) may then be applied to the SMP connector 210, causing the compression flange 214 to shrink or contract back to the contracted state 210a (e.g., return to its original shape), as shown in FIG. 12. Thus, the general process may be seen as training the shape memory material of the SMP connector 210 at an elevated temperature (e.g., injection mold temperature), which results in the contracted state 210a, then deforming the SMP connector 210 (e.g., flaring the compression flange 214 with the expansion tool 250) at a low temperature, and then activating the shape memory material of the SMP connector 210 at a transition temperature. Similarly, this process may be carried out using SMP materials having thermal activation properties, moisture activation properties and the like.

In some aspects of the disclosure, the SMP ring 110 and/or the SMP connector 210 may be formed from a polyurethane SMP material, for example. The polyurethane SMP material may be 3D printed, 4D printed, prepared with a conventional extrusion process, prepared with a conventional molding process, and the like. The SMP material properties may be defined such that the elastic modulus changes at a temperature below a glass transition temperature (e.g., a hard state) and changes at a temperature above the glass transition temperature (e.g., a soft state). Thus, at a temperature higher than the glass transition temperature, the SMP material is shaped by applying a low force or stress and when the force/stress is removed at a temperature below the glass transition temperature, the formed shape is retained. Heating the formed SMP material to a temperature higher than the glass transition temperature while applying no force or stress eliminates the strain from the formed shape and the SMP material changes back to its original shape.

In some aspects of the disclosure, an extrusion grade commercial material may be extruded at varying draw down ratios and internal air pressure to customize the uniaxial orientation of the SMP ring 110 and/or the SMP connector 210. The material type, glass transition temperature, wall thickness, and ability to crystallize may impact the appearance of the part, the response to variation in extrusion parameters, the temperature to initiate shrinkage, the amount of shrinkage and the strength of the part. For example, flexible PVC, TVU or TPE blends containing PP, EVA and/or LDPE can be utilized for the SMP ring 110 and/or the SMP connector 210 (e.g., shrinkable tubing bushing).

Figure 13:
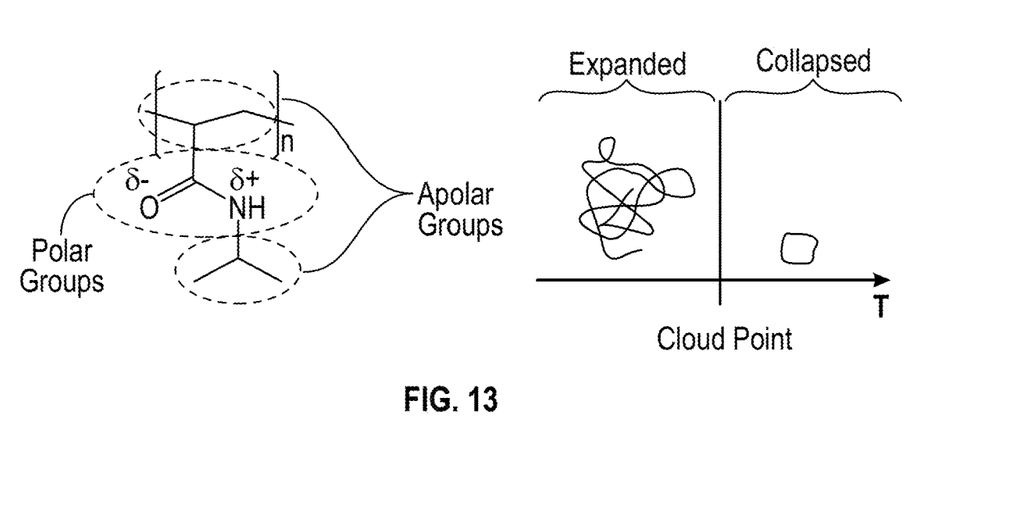
FIG. 13 is a schematic diagram of characteristics of an SMP material, according to aspects of the disclosure.

In some aspects of the disclosure, a custom compound with thermo-responsive material may be extruded. The custom compound may be designed to retain its expanded dimensions out of water bath of the extruder. The cloud point of the material may be designed to allow the initiation of shrink upon losing water or solvent content at increased temperature (e.g, the material starts shrinking as the moisture or solvent comes off). For example, PNIPAAm may be used to tailor these characteristics as shown in FIG. 13. PNIPAAm or like additives with thermos-responsive property may be blended with EVA, Poly (ethylene glycol), TPU, TPE or melt processable polybutadiene, for example.

In some aspects of the disclosure, a material may be designed to form into or get to an expanded state under a lubricating assembly solvent post-extrusion-processing for ease of assembly, and then change to a contracted state upon temperature application.

In some aspects of the disclosure, Polynonborne, a thermoset resin, or other types of thermoset resins might be used for creating SMP ring 110 and/or the SMP connector 210.

In some aspects of the disclosure, polymer miscibility, solvent selection, choice of thermos-responsive material, compound stability during and post-extrusion, choice of "good solvent" may be some variants impacting the thermo-responsive polymer performance of the SMP ring 110 and/or the SMP connector 210.

In some aspects of the disclosure, the type of die and tooling may be variants for uniaxially oriented tubing of the SMP ring 110 and/or the SMP connector 210.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

The invention claimed is:

1. A junction assembly for an intravenous (IV) component, the junction assembly comprising:
    a component connector having a spigot configured to slideably receive an inner surface of an IV tube to form a connector/tube junction; and
    a shaped memory polymer (SMP) ring formed of a shape changing material, the SMP ring comprising:
        an expanded state in which the SMP ring is slideably disposed encircling the connector/tube junction; and
        a contracted state in which the SMP ring is retained in a retaining position squeezing the connector/tube junction,
    wherein the shape changing material is configured to change to one of the expanded state and the contracted state upon being subjected to an external stimuli,
    wherein the spigot includes a barb disposed inward from a tip of the spigot, the barb sized and shaped to provide a friction fit with the inner surface of the IV tube,
    wherein the barb has an outer circumference and the SMP ring has an inner diameter that is narrower than the outer circumference of the barb when the SMP ring is in the contracted state, and
    wherein the entire SMP ring is disposed inward from the barb and does not encircle the barb in the contracted state.

2. The junction assembly of claim 1, wherein the spigot is sized and shaped to provide a friction fit with the inner surface of the IV tube.

3. The junction assembly of claim 1, further comprising one of a solvent bond and an adhesive bond disposed between the spigot and the inner surface of the IV tube.

4. The junction assembly of claim 1, wherein the external stimuli is a change in temperature.

5. The junction assembly of claim 1, wherein the external stimuli is a change in moisture content.

6. The junction assembly of claim 1, wherein the shape changing material is configured to be in the expanded state upon application of a lubricating assembly solvent and to be in the contracted state upon application of a temperature change.

7. The junction assembly of claim 1, wherein the shape changing material is an extruded thermo-responsive material that maintains the expanded state outside of an extrusion water bath, and wherein a cloud point of the thermo-responsive material is configured to shrink the thermo-responsive material to the contracted state upon losing moisture content when an increased temperature is applied.

8. The junction assembly of claim 1, wherein the shape changing material comprises Poly (N-isopropylacrylamide) (PNIPAAm) blended with one of EVA, Poly (ethylene glycol), TPU, TPE or melt processable polybutadiene.

9. The junction assembly of claim 1, wherein the shape changing material comprises a flexible PVC blend containing one of PP, EVA and LDPE.

10. The junction assembly of claim 1, wherein the shape changing material comprises a flexible TPE blend containing one of PP, EVA and LDPE.

11. A junction assembly for an intravenous (IV) component, the junction assembly comprising:
    a shaped memory polymer (SMP) connector formed of a shape changing material, the SMP connector comprising:
        a shaft configured to slideably receive an inner surface of an IV tube;
        a compression flange configured to slideably receive an outer surface of the IV tube, the shaft, the compression flange and the IV tube forming a connector/tube junction; and
        a gap disposed between the shaft and the compression flange,
    wherein in an expanded state the compression flange is expanded by a force at a temperature above a glass transition temperature and the gap at a tube insertion end of the SMP connector is a first width,
    wherein the compression flange remains expanded upon removal of the force at a temperature below the glass transition temperature, and
    wherein in a contracted state the compression flange is narrowed back to an original shape upon raising the temperature above the glass transition temperature and the gap at the tube insertion end of the SMP connector is a second width that is less than the first width, and
    wherein the shape changing material is configured to compress and retain the IV tube within the gap in the contracted state.

12. The junction assembly of claim 11, wherein the compression flange is expanded into the expanded state by a force applied by an expansion tool, and wherein the compression flange is also contracted into the contracted state by application of a change in moisture content to the compression flange.

13. The junction assembly of claim 11, wherein the expanded state of the compression flange is a funnel shape and the contracted state of the compression flange is a cylindrical shape.

14. The junction assembly of claim 11, further comprising one of a solvent bond and an adhesive bond disposed between one of the shaft and the compression flange and the inner surface of the IV tube.

15. The junction assembly of claim 11, wherein the shape changing material comprises Poly (N-isopropylacrylamide) (PNIPAAm) blended with one of EVA, Poly (ethylene glycol), TPU, TPE or melt processable polybutadiene, and wherein a cloud point of the shape changing material is configured to shrink the shape changing material to the contracted state upon losing moisture content when an increased temperature is applied.

16. An infusion set assembly, comprising:
an IV set component;
an IV tube; and
the junction assembly of claim 1 coupling the IV tube to the IV set component,
wherein the junction assembly is configured to allow slideable movement of the IV tube with respect to the component connector when the SMP ring is in an expanded state, and
wherein the junction assembly is configured to retain the IV tube securely to the component connector when the SMP ring is in a contracted state.

17. An infusion set assembly, comprising:
an IV set component;
an IV tube; and
the junction assembly of claim 13 coupling the IV tube to the IV set component.

18. The junction assembly of claim 11, wherein the compression flange is also expanded by a lubricating assembly solvent.

19. The infusion set assembly of claim 17, the compression flange comprising:
a flared shape in the expanded state; and
a cylindrical shape in the contracted state.

* * * * *